United States Patent
Bibulić et al.

(10) Patent No.: US 12,404,267 B2
(45) Date of Patent: Sep. 2, 2025

(54) SOLID STATE FORMS OF N-[2-(2-{4-[2-(6,7-DIMETHOXY-3,4-DIHYDRO-2(1H)-ISOQUINOLINYL)ETHYL]PHENYL}-2H-TETRAZOL-5-YL)-4,5-DIMETHOXYPHENYL]-4-OXO-4H-CHROMENE-2-CARBOXAMIDE AND OF ITS MESYLATE SALT

(71) Applicant: ASSIA CHEMICAL INDUSTRIES LTD., Tel Aviv (IL)

(72) Inventors: Petar Bibulić, Zagreb (HR); Dijana Škalec Šamec, Jastrebarsko (HR); Marina Marinkovic, Sesvete-Zagreb (HR); Jasna Dogan, Petrinja (HR)

(73) Assignee: ASSIA CHEMICAL INDUSTRIES LTD., Tel Aviv (IL)

(*) Notice: Subject to any disclaimer, the term of this patent is extended or adjusted under 35 U.S.C. 154(b) by 938 days.

(21) Appl. No.: 17/429,968

(22) PCT Filed: Feb. 14, 2020

(86) PCT No.: PCT/US2020/018204
§ 371 (c)(1),
(2) Date: Aug. 11, 2021

(87) PCT Pub. No.: WO2020/168144
PCT Pub. Date: Aug. 20, 2020

(65) Prior Publication Data
US 2022/0135548 A1    May 5, 2022

Related U.S. Application Data

(60) Provisional application No. 62/930,044, filed on Nov. 4, 2019, provisional application No. 62/885,846, filed on Aug. 13, 2019, provisional application No. 62/820,900, filed on Mar. 20, 2019, provisional application No. 62/805,425, filed on Feb. 14, 2019.

(51) Int. Cl.
C07D 405/14    (2006.01)
A61K 31/4725   (2006.01)
A61K 45/06     (2006.01)

(52) U.S. Cl.
CPC ........ *C07D 405/14* (2013.01); *A61K 31/4725* (2013.01); *A61K 45/06* (2013.01); *C07B 2200/13* (2013.01)

(58) Field of Classification Search
CPC ................ C07D 405/14; C07D 405/12; A61K 31/4725; A61K 45/06; C07B 2200/13; A61P 35/00
See application file for complete search history.

(56) References Cited

FOREIGN PATENT DOCUMENTS

WO    WO-2014092489 A1 *  6/2014   ........... A61K 31/337

OTHER PUBLICATIONS

Mino R. Caira, "Crystalline Polymorphism of Organic Compounds", Topics in Current Chemistry, vol. 198, pp. 163-208 (1998).
Stephen Byrn et al., "Pharmaceutical Solids: A Strategic Approach to Regulatory Considerations", Pharmaceutical Research, vol. 12, No. 7, pp. 945-954 (1995).
International Search Report and Written Opinion of the International Searching Authority issued in corresponding application PCT/US2020/018204 mailed Jul. 6, 2020 (16 pages).

* cited by examiner

*Primary Examiner* — James H Alstrum-Acevedo
*Assistant Examiner* — Chantal Adlam
(74) *Attorney, Agent, or Firm* — Carter, DeLuca & Farrell LLP

(57) ABSTRACT

The present disclosure relates to solid state forms of Encequidar (previously referred to as HM-30181A) base, Encequidar ((HM-30181A) mesylate, co-crystals of Encequidar (HM-30181A) mesylate, processes for preparation thereof, as well as pharmaceutical compositions including the same.

14 Claims, 11 Drawing Sheets

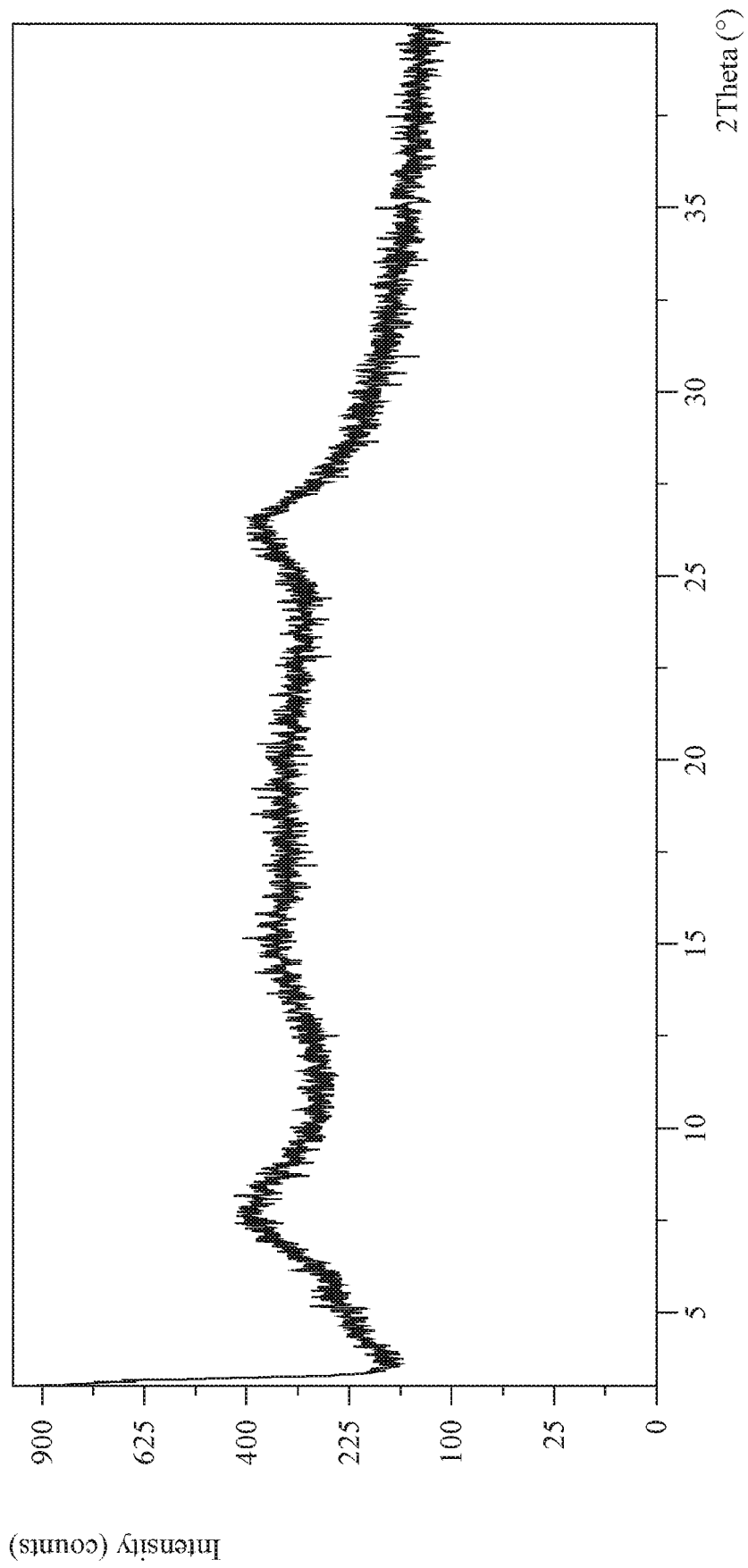
Figure 1. A PXRD of amorphous HM-30181A mesylate.

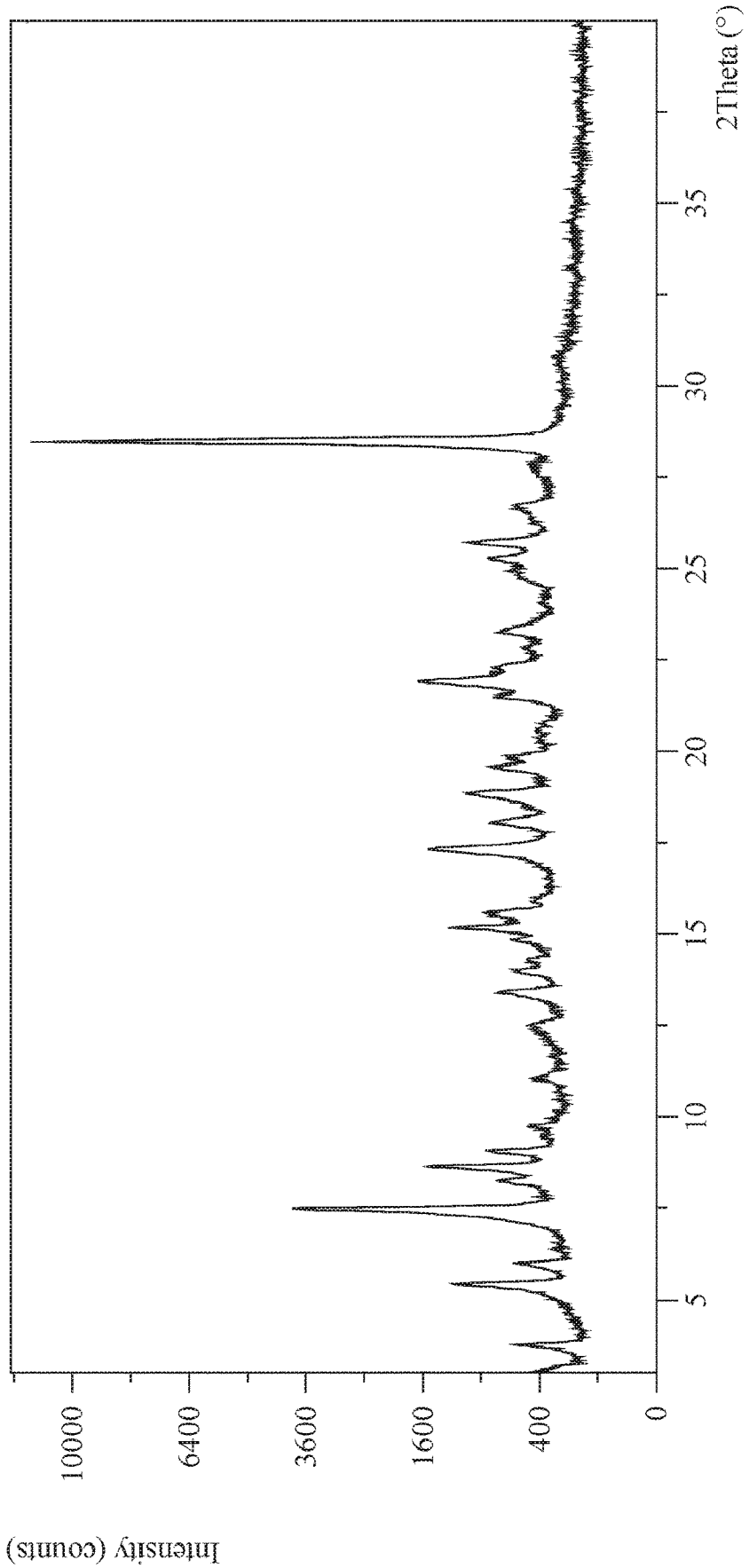

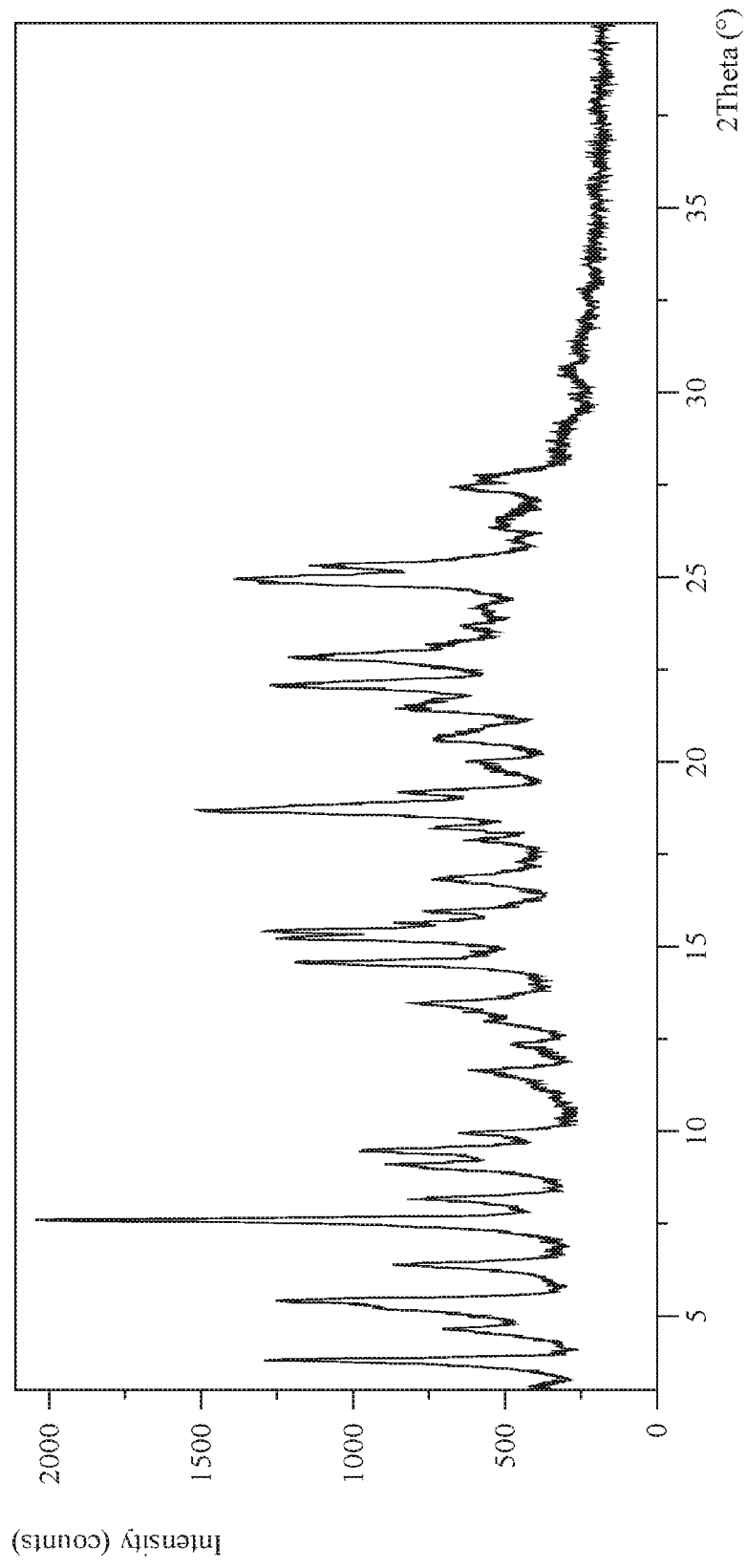
Figure 3: A PXRD of crystalline HM-30181A mesylate form B

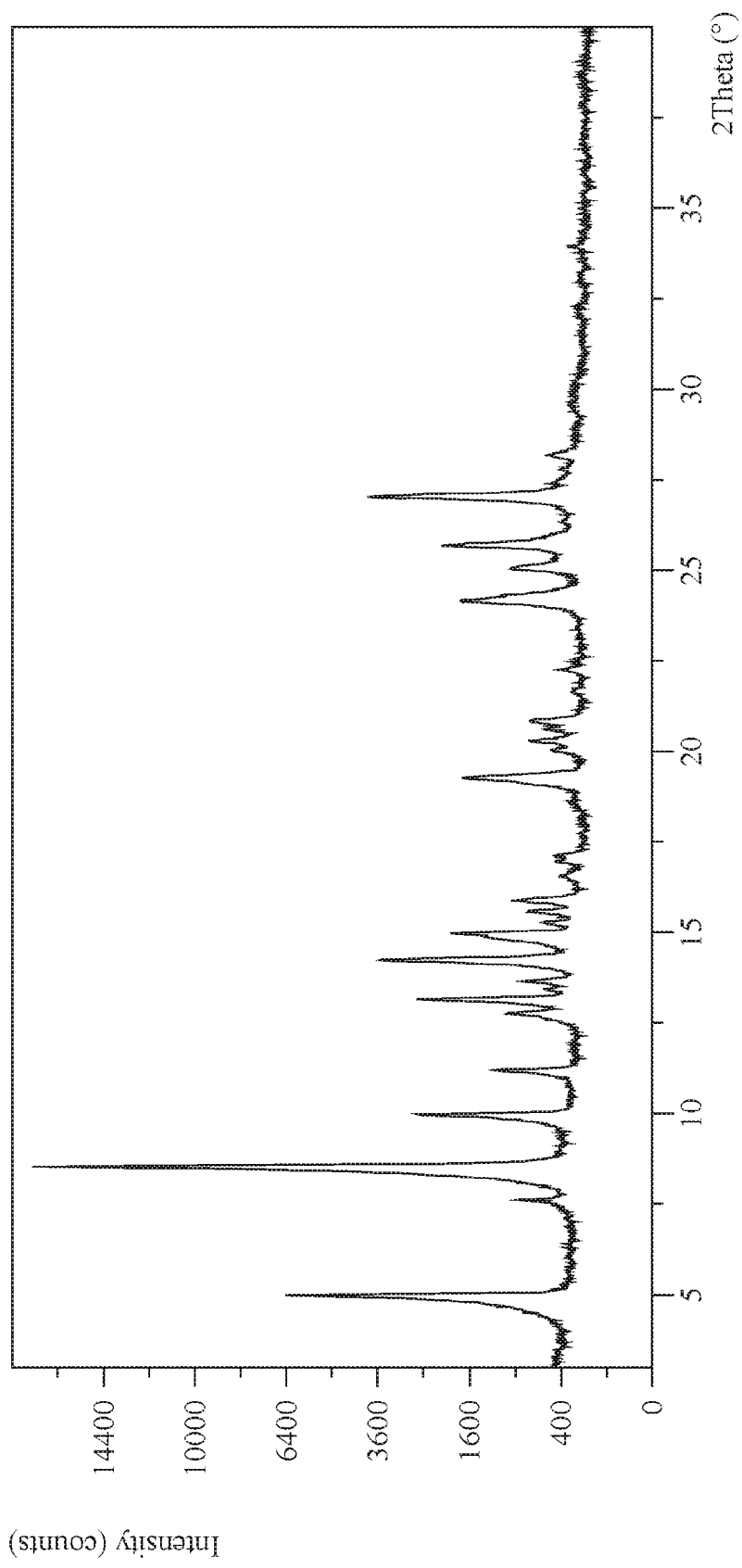

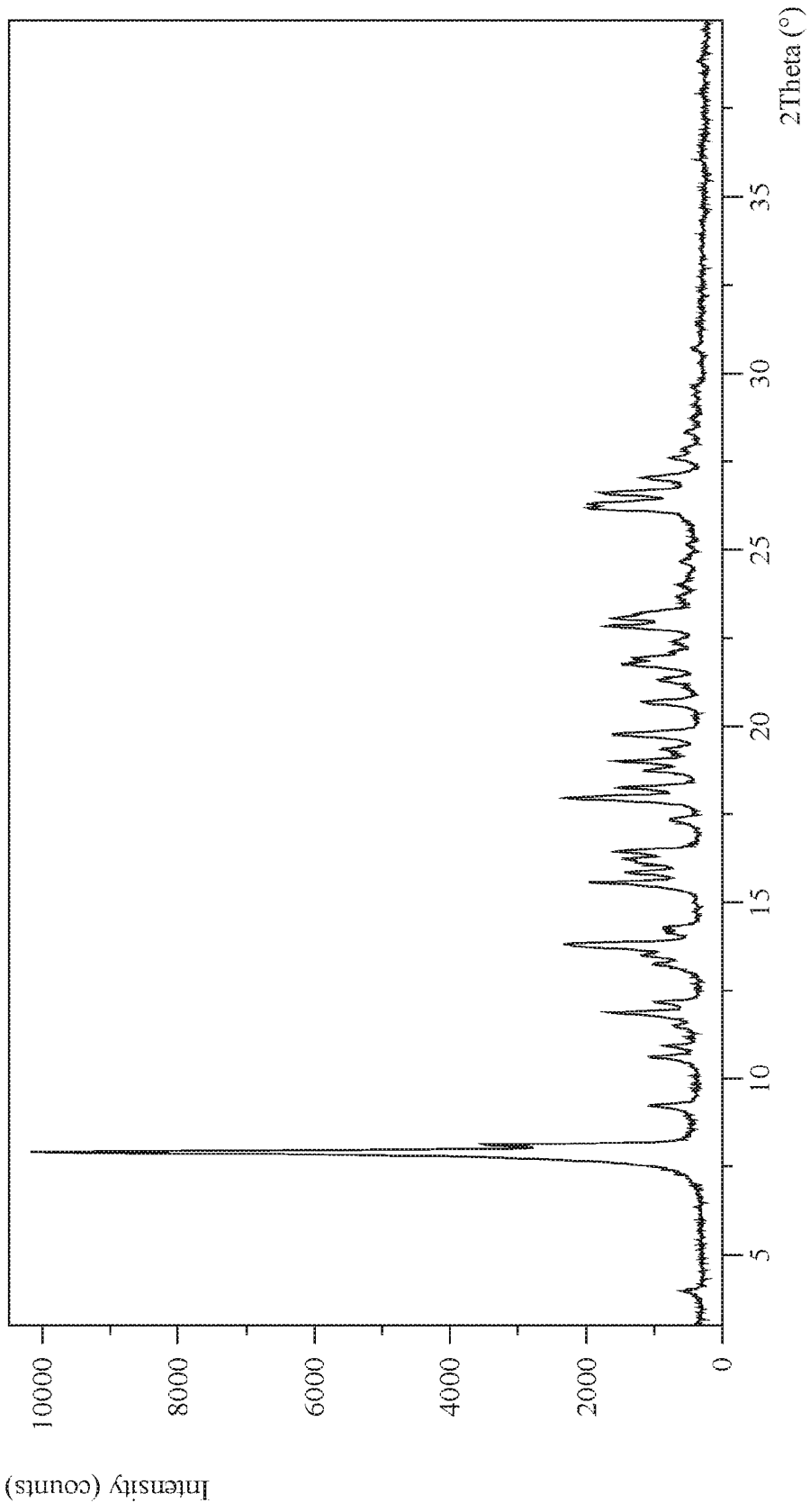

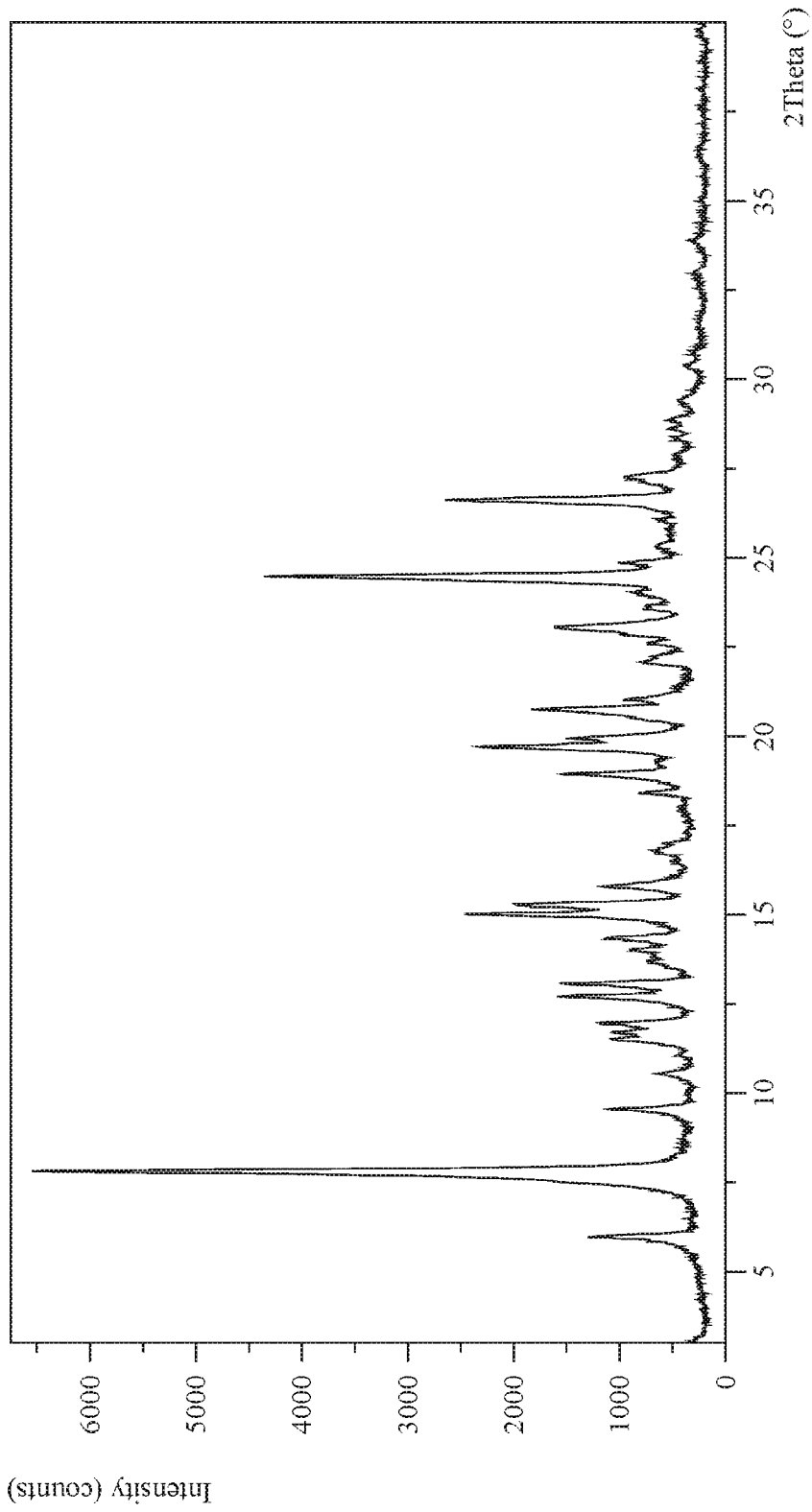
Figure 6: A PXRD of co-crystal of HM-30181A mesylate and nicotinamide

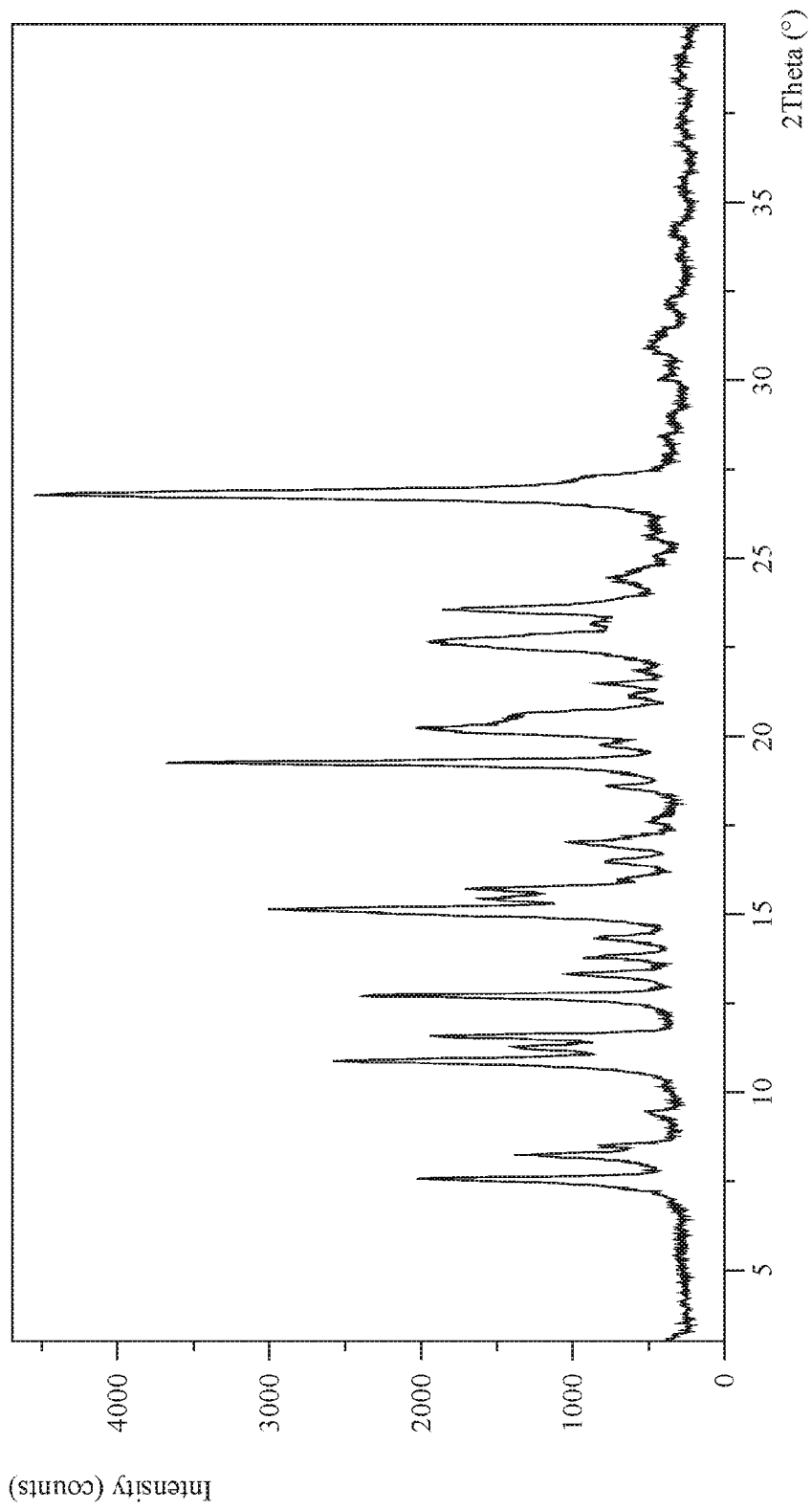
Figure 7. A PXRD of co-crystal of HM-30181A mesylate and citric acid

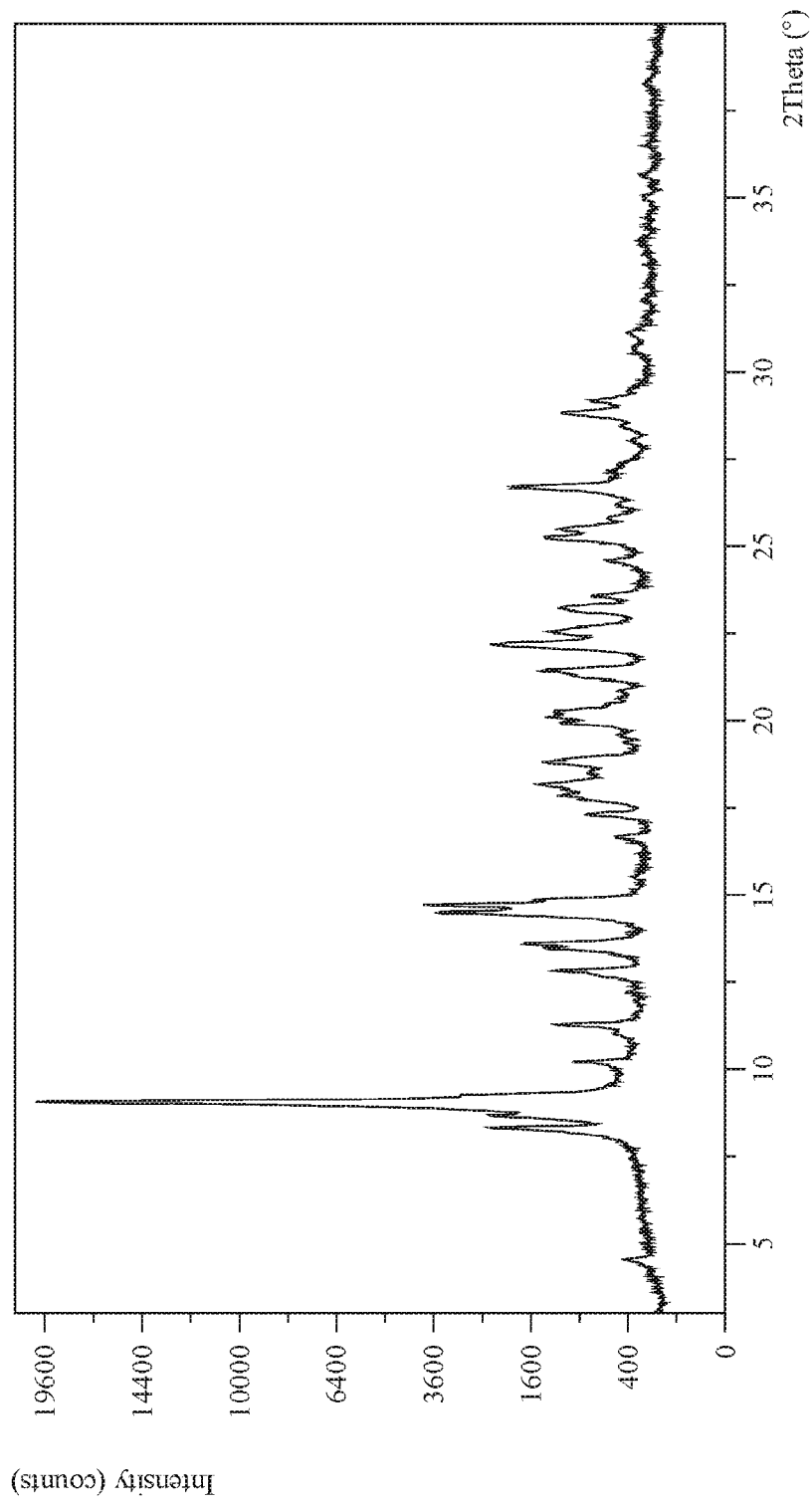
Figure 8: A PXRD of crystalline Encequidar (HM-30181A) mesylate Form Y

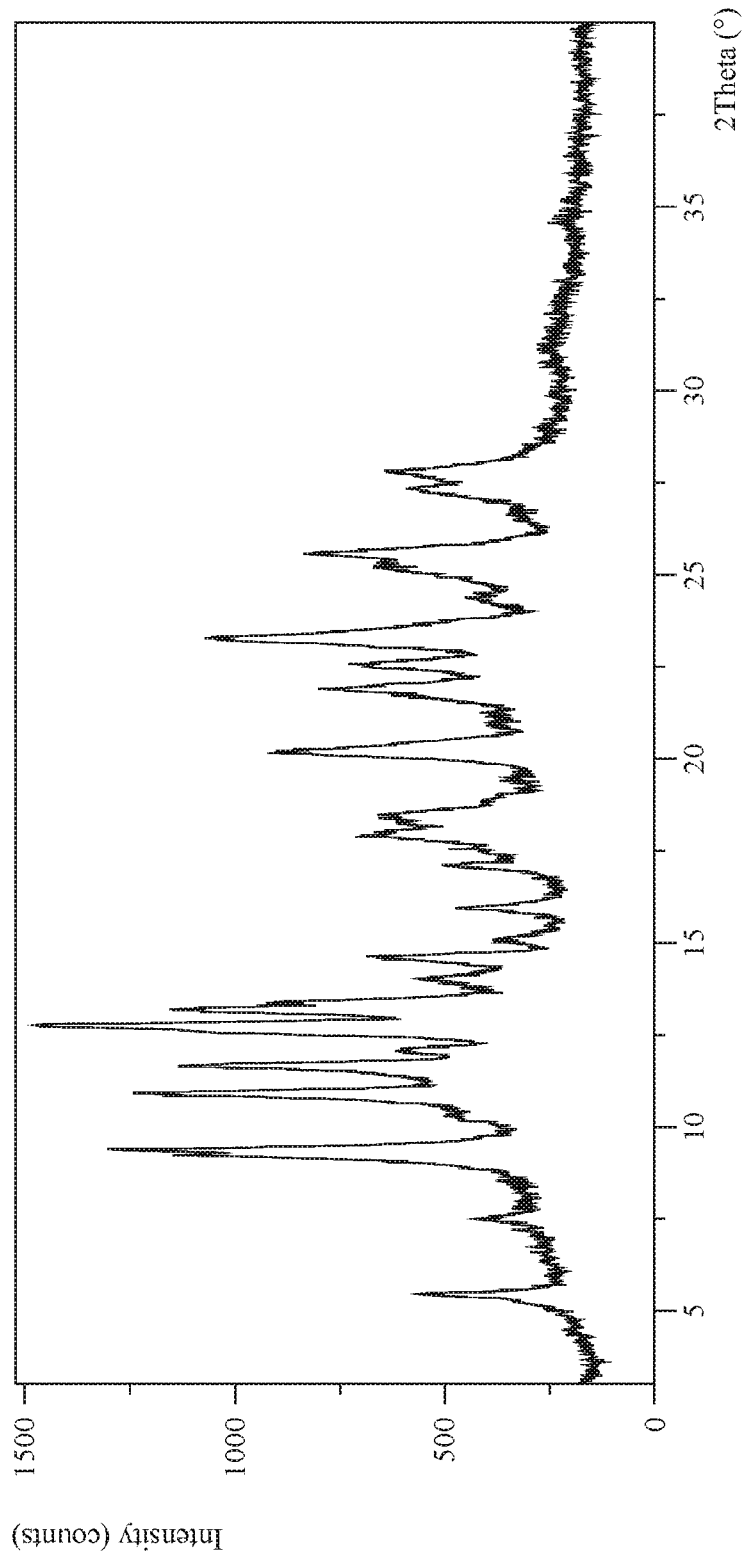
Figure 9: A PXRD of crystalline Encequidar (HM-30181A) mesylate Form J

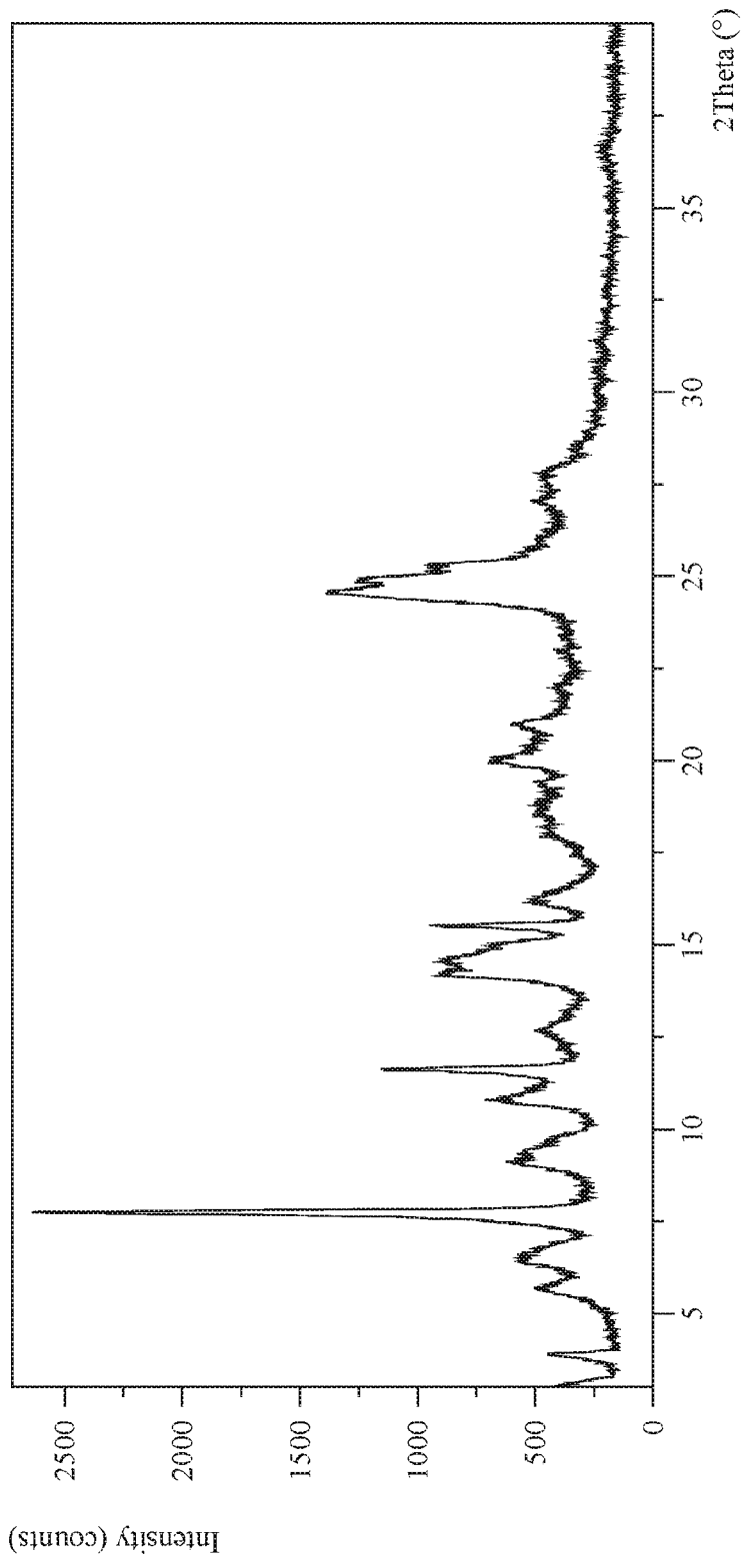
Figure 10: A PXRD of crystalline Encequidar (HM-30181A) mesylate Form E

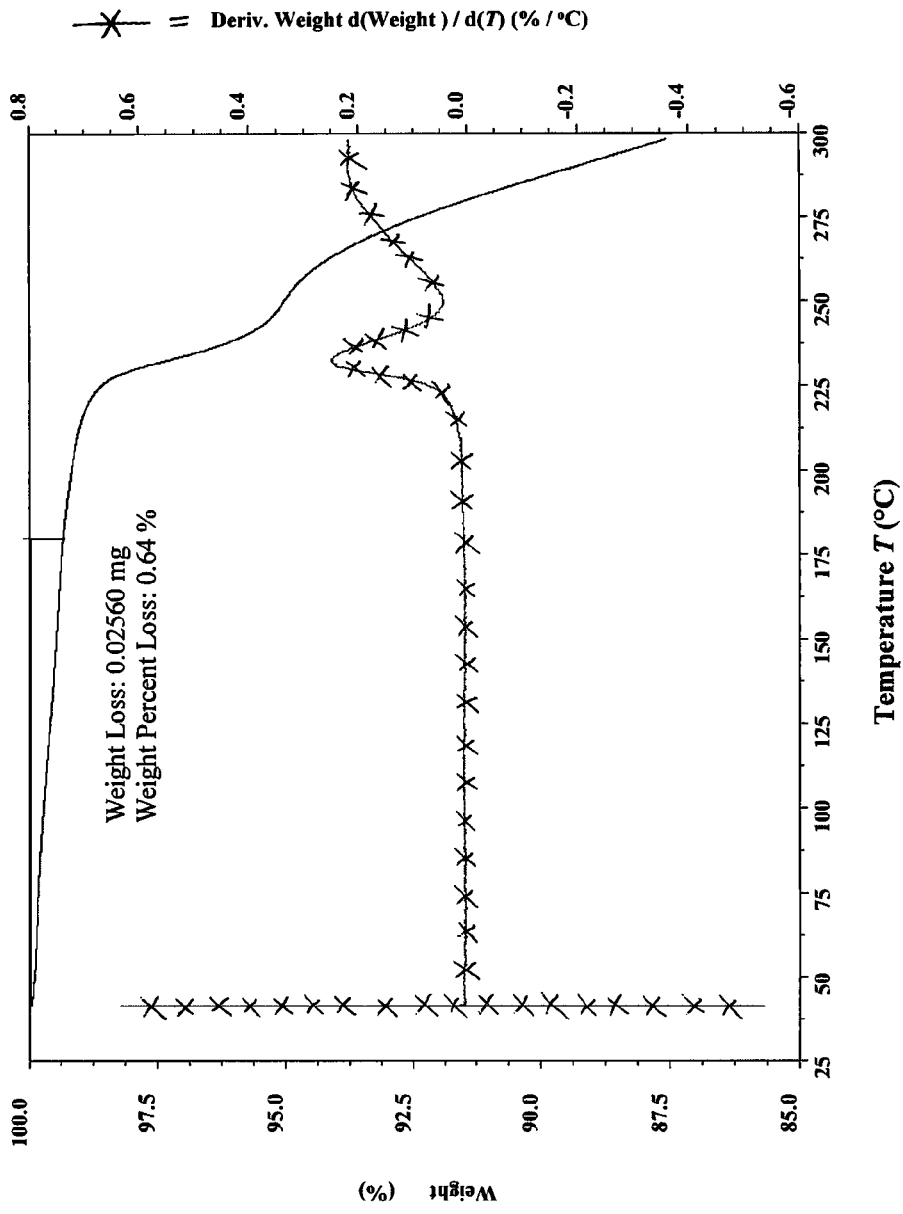
Figure 11: A TGA thermogram of crystalline Encequidar (HM-30181A) mesylate Form B

SOLID STATE FORMS OF N-[2-(2-{4-[2-(6,7-DIMETHOXY- 3,4-DIHYDRO-2(1H)-ISOQUINOLINYL)ETHYL]PHENYL}-2H-TETRAZOL-5-YL)-4,5-DIMETHOXYPHENYL]-4-OXO-4H-CHROMENE-2-CARBOXAMIDE AND OF ITS MESYLATE SALT

CROSS REFERENCE TO RELATED APPLICATIONS

This application is a National Stage of, and claims priority to and the benefit of, International Patent Application No. PCT/US2020/018204 filed Feb. 14, 2020, which, in turn, claims the benefit of and priority to, U.S. Provisional Patent Application No. 62/805,425, filed Feb. 14, 2019, U.S. Provisional Patent Application No. 62/820,900, filed Mar. 20, 2019, U.S. Provisional Patent Application No. 62/885,846, filed Aug. 13, 2019, and U.S. Provisional Patent Application No. 62/930,044, filed Nov. 4, 2019, the entire disclosures of each of which are incorporated by reference herein.

TECHNICAL FIELD

The present disclosure relates to solid state forms of Encequidar (previously referred to as HM-30181A) base, Encequidar (HM-30181A) mesylate, co-crystals of Encequidar (HM-30181A) mesylate, processes for preparation thereof, as well as pharmaceutical compositions including the same.

The present disclosure also relates to synthetic processes for preparing Encequidar (HM-30181A).

BACKGROUND

Encequidar has the chemical name N-[2-(2-{4-[2-(6,7-Dimethoxy-3,4-dihydro-2(1H)-isoquinolinyl)ethyl]phenyl}-2H-tetrazol-5-yl)-4,5-dimethoxyphenyl]-4-oxo-4H-chromene-2-carboxamide, and the code name HM-30181A. Encequidar (HM-30181A) has the following chemical structure:

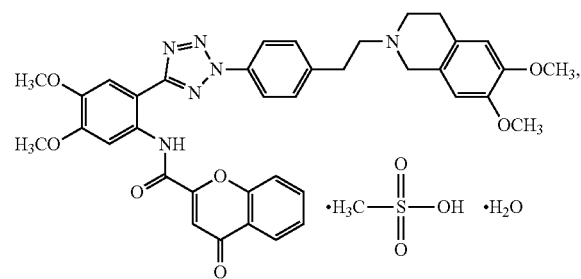

Encequidar (HM-30181A) is being developed as a combination with Paclitaxel, indicated for the treatment of metastatic breast cancer and gastric cancer. Encequidar (HM-30181A) is disclosed in U.S. Pat. No. 7,625,926 (counterpart of International Publication No. WO 2005/033097). International Publication No. WO 2011/087316 discloses a process for preparing Encequidar (HM-30181A) and its mesylate salt, which includes use of a benzothiazolylthioester in the final acylation step.

Solid state forms of Encequidar (HM-30181A) and its mesylate salt are disclosed in International Publication No. WO 2014/092489.

Polymorphism, the occurrence of different crystal forms, is a property of some molecules and molecular complexes. A single compound, like Encequidar (HM-30181A) or salt thereof, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms and co-crystals) of an active pharmaceutical ingredient may possess different properties. Such variations in the properties of different salts and solid state forms, co-crystals and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms, co-crystals and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms, co-crystals and solvates of a pharmaceutical product can provide materials having desirable processing properties, such as ease of handling, ease of processing, storage stability, and ease of purification, or as desirable intermediate crystal forms that facilitate conversion to other salts or polymorphic forms. New salts, polymorphic forms, co-crystals and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

SUMMARY

The present disclosure relates to solid state forms of Encequidar (HM-30181A) base, Encequidar (HM-30181A), co-crystals of Encequidar (HM-30181A) mesylate, and to processes for preparation thereof, and to pharmaceutical compositions including these solid state forms or combinations thereof.

The present disclosure also provides uses of the solid state forms and co-crystals of Encequidar (HM-30181A) base and Encequidar (HM-30181A) mesylate for preparing other solid state forms of Encequidar (HM-30181A) base, Encequidar (HM-30181A) mesylate, other co-crystals and/or salts of Encequidar (HM-30181A), and their solid state forms thereof.

In another embodiment, the present disclosure encompasses the herein described solid state forms and co-crystals of Encequidar (HM-30181A) base and Encequidar (HM-30181A) mesylate for use in the preparation of pharmaceutical compositions and/or formulations, particularly as a combination with additional active agents, such as Paclitaxel, in some embodiments for the treatment of cancer, or in some embodiments, for the treatment of metastatic breast cancer and/or gastric cancer.

Another embodiment the present disclosure encompasses the use of the herein described solid state forms and co-crystals of Encequidar (HM-30181A) base and Encequidar (HM-30181A) mesylate for the preparation of pharmaceutical compositions and/or formulations. The pharmaceutical compositions and/or formulations can be in combination with additional active agents, such as Paclitaxel.

The present disclosure further provides pharmaceutical compositions including solid state forms and co-crystals of Encequidar (HM-30181A) base and Encequidar (HM-30181A) mesylate. The pharmaceutical compositions and/or formulations can be in combination with additional active agents, such as Paclitaxel.

In yet another embodiment, the present disclosure encompasses pharmaceutical formulations including any one or a combination of the solid state forms and co-crystals of Encequidar (HM-30181A) base and Encequidar (HM-30181A) mesylate and at least one pharmaceutically acceptable excipient. The pharmaceutical composition or formulation includes oral dosage forms, e.g., a tablet or capsule, and can be in combination with additional active agents, such as Paclitaxel The present disclosure encompasses processes to prepare said pharmaceutical formulations of solid state forms and co-crystals of Encequidar (HM-30181A) base and Encequidar (HM-30181A) mesylate, including combining any one or a combination of the solid state forms of Encequidar (HM-30181A) mesylate according to the present disclosure with at least one pharmaceutically acceptable excipient. The process can optionally include adding additional active agent(s).

The solid state forms and co-crystals of Encequidar (HM-30181A) base and Encequidar (HM-30181A) mesylate, as well as the pharmaceutical compositions or formulations of solid state forms of Encequidar (HM-30181A) mesylate according to the present disclosure, particularly combination with additional active agents, such as Paclitaxel, can be used as medicaments, in embodiments for the treatment of cancer, or in embodiments for the treatment of metastatic breast cancer and/or gastric cancer.

The present disclosure also provides methods of treating metastatic breast cancer and/or gastric cancer by administering a therapeutically effective amount of any one or a combination of the solid state forms and co-crystals of Encequidar (HM-30181A) base and Encequidar (HM-30181A) mesylate according to the present disclosure, or at least one of the above pharmaceutical compositions or formulations, optionally as a combination with additional active agents, such as Paclitaxel, to a subject suffering from cancer, or to a subject suffering from metastatic breast cancer and/or gastric cancer, or otherwise in need of treatment.

The present disclosure also provides uses of solid state forms and co-crystals of Encequidar (HM-30181A) base and Encequidar (HM-30181A) mesylate of the present disclosure, or at least one of the above pharmaceutical compositions or formulations, for the manufacture of a medicament for treating cancer, or for the manufacture of a medicament for treating metastatic breast cancer and/or gastric cancer. The medicament can be a combination with additional active agents, such as Paclitaxel.

BRIEF DESCRIPTION OF THE FIGURES

FIG. 1 shows a powder X-ray diffraction pattern ("powder XRD" or "PXRD") of amorphous Encequidar (HM-30181A) mesylate.

FIG. 2 shows a PXRD of crystalline Encequidar (HM-30181A) mesylate Form A.

FIG. 3 shows a PXRD of crystalline Encequidar (HM-30181A) mesylate Form B.

FIG. 4 shows a PXRD of crystalline Encequidar (HM-30181A) base Form I.

FIG. 5 shows a PXRD of co-crystal of Encequidar (HM-30181A) mesylate and R-mandelic acid.

FIG. 6 shows a PXRD of co-crystal of Encequidar (HM-30181A) mesylate and nicotinamide.

FIG. 7 shows a PXRD of co-crystal of Encequidar (HM-30181A) mesylate and citric acid.

FIG. 8 shows a PXRD of crystalline Encequidar (HM-30181A) mesylate Form Y.

FIG. 9 shows a PXRD of crystalline Encequidar (HM-30181A) mesylate Form J.

FIG. 10 shows a PXRD of crystalline Encequidar (HM-30181A) mesylate Form E.

FIG. 11 shows a TGA thermogram of crystalline Encequidar (HM-30181A) mesylate Form B.

DETAILED DESCRIPTION

The present disclosure relates to solid state forms of Encequidar (HM-30181A) base and Encequidar (HM-30181A) mesylate, to processes for preparation thereof, and to pharmaceutical compositions including these solid state forms or combinations thereof.

The present disclosure also relates to synthetic processes for preparing Encequidar (HM-30181A).

The terms "Encequidar", "HM-30181A" and "Encequidar (HM-30181A)" may be used interchangeably throughout the disclosure.

The solid state forms of Encequidar (HM-30181A) base and Encequidar (HM-30181A) mesylate according to the present disclosure may have advantageous properties including at least one of: chemical or polymorphic purity, flowability, solubility, dissolution rate, bioavailability, morphology or crystal habit, stability such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Encequidar (HM-30181A) referred to herein as being characterized by graphical data "as depicted in" a Figure will thus be understood to include any crystal forms of the Encequidar (HM-30181A), characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state forms of Encequidar (HM-30181A) or Encequidar (HM-30181A) salt, such as mesylate described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state forms of Encequidar (HM-30181A) or Encequidar (HM-30181A) salt, such as mesylate. Accordingly, in some embodiments of the disclosure, the described solid state forms of Encequidar (HM-30181A) or Encequidar (HM-30181A) salt, such as mesylate may contain from about 1% to about 20% (w/w), from about 5% to about 20% (w/w), or from about 5% to about 10% (w/w) of one or more other solid state forms of the same solid state forms of Encequidar (HM-30181A) or Encequidar (HM-30181A) salt, such as mesylate.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

As used herein, unless stated otherwise, PXRD peaks reported herein are preferably measured using CuK$_\alpha$ radiation, $\lambda$=1.5418 Å.

As used herein, the term "isolated" in reference to solid state forms, salts and a co-crystal with Encequidar (HM-30181A) of the present disclosure corresponds to solid state forms of Encequidar (HM-30181A), Encequidar (HM-30181A) salts or a co-crystal with Encequidar (HM-30181A) that are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

The present disclosure includes solid state forms of Encequidar (HM-30181A) base or Encequidar (HM-30181A) salts, particularly solid state forms of Encequidar (HM-30181A) mesylate.

The present disclosure further includes a crystalline form of Encequidar (HM-30181A) base designated as Form I. Form I of Encequidar (HM-30181A) base can be characterized by data selected from one or more of the following: a PXRD pattern having peaks at 5.0, 8.5, 13.2, 14.3 and 27.0 degrees 2-theta±0.2 degrees 2-theta; a PXRD pattern as depicted in FIG. 4; or combinations of these data.

Form I of Encequidar (HM-30181A) base may be further characterized by a PXRD pattern having peaks at 5.0, 8.5, 13.2, 14.3 and 27.0 degrees 2-theta±0.2 degrees 2-theta, and also having one, two, three, four or five additional peaks at 10.0, 15.0, 19.3, 24.1 and 25.7 degrees 2-theta±0.2 degrees 2-theta.

Form I of Encequidar (HM-30181A) base may alternatively be characterized by a PXRD pattern having peaks at 5.0, 8.5, 10.0, 13.2, 14.3, 15.0, 19.3, 24.1, 25.7 and 27.0 degrees 2-theta±0.2 degrees 2-theta.

Form I of Encequidar (HM-30181A) base may be characterized by each of the above characteristics alone or by all possible combinations, e.g., by a PXRD pattern having peaks at 5.0, 8.5, 13.2, 14.3 and 27.0 degrees 2-theta±0.2 degrees 2-theta and a PXRD pattern as depicted in FIG. 4.

The present disclosure further includes a crystalline form of Encequidar (HM-30181A) mesylate designated as Form A. Form A of Encequidar (HM-30181A) mesylate can be characterized by data selected from one or more of the following: a PXRD pattern having peaks at 5.4, 7.5, 8.7, 17.4 and 21.9 degrees 2-theta±0.2 degrees 2-theta; a PXRD pattern as depicted in FIG. 2; or combinations of these data.

Form A of Encequidar (HM-30181A) mesylate may be further characterized by a PXRD pattern having peaks at 5.4, 7.5, 8.7, 17.4 and 21.9 degrees 2-theta±0.2 degrees 2-theta, and also having one, two, three, four or five additional peaks at 15.2, 15.6, 18.9, 21.5 and 25.7 degrees 2-theta±0.2 degrees 2-theta.

Form A of Encequidar (HM-30181A) mesylate may alternatively be characterized by a PXRD pattern having peaks at 5.4, 7.5, 8.7, 15.2, 15.6, 17.4, 18.9, 21.5, 21.9 and 25.7 degrees 2-theta±0.2 degrees 2-theta.

Form A of Encequidar (HM-30181A) mesylate may be characterized by each of the above characteristics alone/or by all possible combinations, e.g., by a PXRD pattern having peaks at 5.4, 7.5, 8.7, 17.4 and 21.9 degrees 2-theta±0.2 degrees 2-theta and a PXRD pattern as depicted in FIG. 2.

The present disclosure further includes a crystalline form of Encequidar (HM-30181A) mesylate designated as Form B. Form B of Encequidar (HM-30181A) mesylate can be characterized by data selected from one or more of the following: a PXRD pattern having peaks at 6.4, 7.6, 9.5, 14.6 and 18.7 and 25.0 degrees 2-theta±0.2 degrees 2-theta; a PXRD pattern as depicted in FIG. 3; or combinations of these data.

Form B of Encequidar (HM-30181A) mesylate may be further characterized by a PXRD pattern having peaks at 6.4, 7.6, 9.5, 14.6, 18.7 and 25.0 degrees 2-theta±0.2 degrees 2-theta, and also having one, two, three, four or five additional peaks at 4.6, 10.0, 15.4, 17.9 and 22.8 degrees 2-theta±0.2 degrees 2-theta.

Form B of Encequidar (HM-30181A) mesylate may alternatively be characterized by a PXRD pattern having peaks at 4.6, 6.4, 7.6, 9.5, 10.0, 14.6, 15.4, 17.9, 18.7, 22.8 and 25.0 degrees 2-theta±0.2 degrees 2-theta. In embodiments, Form B of Encequidar (HM-30181A) mesylate may be characterized by a PXRD pattern having peaks at 3.8, 4.6, 5.4, 6.4, 7.6, 8.2, 9.1, 9.5, 9.9, 11.7, 12.4, 13.5, 14.6, 15.2, 15.4, 16.0, 16.8, 17.9, 18.2, 18.7, 19.2, 20.0, 20.6, 21.4, 22, 22.8, 25.0, 25.3, 26.4, and 27.4 degrees 2-theta±0.2 degrees 2-theta.

In any of the above described embodiments of Form B, the said Form B may be further characterized by a PXRD which having an absence of a peak at 7.9 degrees 2-theta±0.2 degrees 2-theta.

Thus, in an embodiment, form B of Encequidar (HM-30181A) mesylate can be characterized by data selected from one or more of the following: a PXRD pattern having peaks at 6.4, 7.6, 9.5, 14.6 and 18.7 and 25.0 degrees 2-theta±0.2 degrees 2-theta, and an absence of a peak at 7.9 degrees 2-theta±0.2 degrees 2-theta. Form B of Encequidar (HM-30181A) mesylate may be further characterized by a PXRD pattern having peaks at 6.4, 7.6, 9.5, 14.6 and 18.7 and 25.0 degrees 2-theta±0.2 degrees 2-theta, and an absence of a peak at 7.9 degrees 2-theta±0.2 degrees 2-theta, and also having one, two, three, four or five additional peaks at 4.6, 10.0, 15.4, 17.9 and 22.8 degrees 2-theta±0.2 degrees 2-theta. Form B of Encequidar (HM-30181A) mesylate may alternatively be characterized by a PXRD pattern having peaks at 4.6, 6.4, 7.6, 9.5, 10.0, 14.6, 15.4, 17.9, 18.7, 22.8 and 25.0 degrees 2-theta±0.2 degrees 2-theta and an absence of a peak at 7.9 degrees 2-theta±0.2 degrees 2-theta. Alternatively, Form B of Encequidar (HM-30181A) mesylate may be characterized by a PXRD pattern having peaks at 3.8, 4.6, 5.4, 6.4, 7.6, 8.2, 9.1, 9.5, 9.9, 11.7, 12.4, 13.5, 14.6, 15.2, 15.4, 16.0, 16.8, 17.9, 18.2, 18.7, 19.2, 20.0, 20.6, 21.4, 22, 22.8, 25.0, 25.3, 26.4, and 27.4 degrees 2-theta±0.2 degrees 2-theta, and an absence of a peak at 7.9 degrees 2-theta±0.2 degrees 2-theta.

The present disclosure further includes a crystalline form of Encequidar (HM-30181A) mesylate Form B, which can be characterized by data selected from one or more of the following: a PXRD pattern having peaks at 6.4, 7.6, 9.5, 14.6 and 18.7 and 25.0 degrees 2-theta±0.2 degrees 2-theta, and an absence of a peak at 7.9 degrees 2-theta±0.2 degrees 2-theta; a PXRD pattern as depicted in FIG. 3; or combinations of these data In specific embodiments, Form B of Encequidar (HM-30181A) mesylate may be characterized by a PXRD pattern having peaks according to the following peak list specified in Table 1:

TABLE 1

| Form B | |
|---|---|
| Peak position, °2 theta | Relative peak Intensity, % |
| 3.8 | 59 |
| 4.6 | 23 |
| 5.4 | 57 |
| 6.4 | 32 |
| 7.6 | 100 |
| 8.2 | 26 |
| 9.1 | 34 |
| 9.5 | 41 |
| 10.0 | 22 |
| 11.7 | 17 |
| 12.4 | 11 |
| 13.5 | 28 |
| 14.6 | 53 |
| 15.2 | 57 |
| 15.4 | 60 |
| 16.0 | 27 |
| 16.8 | 25 |
| 17.9 | 18 |
| 18.2 | 25 |
| 18.7 | 72 |
| 19.2 | 31 |
| 20.0 | 19 |
| 20.6 | 26 |
| 21.4 | 30 |
| 22.0 | 56 |
| 22.8 | 50 |
| 25.0 | 63 |
| 25.3 | 46 |
| 26.4 | 13 |
| 27.4 | 21 |

Form B of Encequidar (HM-30181A) mesylate according to any embodiment of the invention may be an anhydrous form. In embodiments, Form B of Encequidar (HM-30181A) mesylate has a weight loss of about 0.64% (w/w) at temperature of up to about 180° C., as measured by TGA. A TGA thermogram as depicted in FIG. 11.

Form B of Encequidar (HM-30181A) mesylate may be characterized by each of the above characteristics alone or by all possible combinations, e.g., by a PXRD pattern having peaks at 6.4, 7.6, 9.5, 14.6 and 18.7 and 25.0 degrees 2-theta±0.2 degrees 2-theta and also a PXRD pattern as depicted in FIG. 3.

Form B of Encequidar (HM-30181A) mesylate may have advantageous properties as discussed above. Particularly, form B of Encequidar (HM-30181A) mesylate may have advantageous solubility. For example, Form B of Encequidar mesylate has a solubility which is surprisingly greater than the solubility of amorphous Encequidar mesylate. Low solubility of Encequidar and the resulting difficulties in its formulating in order to achieve aproper absorption rate is discussed in WO 2014/092489, where it is taught to formulate the API as a solid dispersion in a water soluble polymer. The present Form B of Encequidar mesylate provides an opportunity for the API to be formulated without the use of special polymers or complicating the formulation process by preparing a solid dispersion.

The present disclosure further includes a crystalline form of Encequidar (HM-30181A) mesylate designated as Form Y. Form Y of Encequidar (HM-30181A) mesylate can be characterized by data selected from one or more of the following: a PXRD pattern having peaks at 9.1, 10.2, 11.3, 12.8 and 14.7 degrees 2-theta±0.2 degrees 2-theta; a PXRD pattern as depicted in FIG. 8; or combinations of these data.

Form Y of Encequidar (HM-30181A) mesylate may be further characterized by a PXRD pattern having peaks at 9.1, 10.2, 11.3, 12.8 and 14.7 degrees 2-theta±0.2 degrees 2-theta, and also having one, two, three, four or five additional peaks at 8.3, 17.3, 21.4, 23.2 and 26.7 degrees 2-theta±0.2 degrees 2-theta.

Form Y of Encequidar (HM-30181A) mesylate may be a solvate, particularly an acetic acid solvate.

Form Y of Encequidar (HIM-30181A) mesylate may alternatively be characterized by a PXRD pattern having peaks at 8.3, 9.1, 10.2, 11.3, 12.8 and 14.7, 17.3, 21.4, 23.2 and 26.7 degrees 2-theta±0.2 degrees 2-theta.

Form Y of Encequidar (HM-30181A) mesylate may be characterized by each of the above characteristics alone or by all possible combinations, e.g., by a PXRD pattern having peaks 9.1, 10.2, 11.3, 12.8 and 14.7 and 25.0 degrees 2-theta±0.2 degrees 2-theta and a PXRD pattern as depicted in FIG. 8.

The present disclosure further includes a crystalline form of Encequidar (HM-30181A) mesylate designated as Form J. Form J of Encequidar (HM-30181A) mesylate can be characterized by data selected from one or more of the following: a PXRD pattern having peaks at 9.2, 10.9, 11.7, 12.8 and 13.2 degrees 2-theta±0.2 degrees 2-theta; a PXRD pattern as depicted in FIG. 9 or combinations of these data.

Form J of Encequidar (HM-30181A) mesylate may be an anhydrous form.

Form J of Encequidar (HM-30181A) mesylate may be characterized by each of the above characteristics alone or by all possible combinations, e.g., by a PXRD pattern having peaks 9.2, 10.9, 11.7, 12.8 and 13.2 degrees 2-theta±0.2 degrees 2-theta and a PXRD pattern as depicted in FIG. 9.

The present disclosure further includes a crystalline form of Encequidar (HM-30181A) mesylate designated as Form E. Form E of Encequidar (HM-30181A) mesylate can be characterized by data selected from one or more of the following: a PXRD pattern having peaks at 3.9, 7.8, 11.7, 15.5 and 24.6 degrees 2-theta±0.2 degrees 2-theta; a PXRD pattern as depicted in FIG. 10; or combinations of these data.

Form E of Encequidar (HM-30181A) mesylate may be a solvate, particularly a methanol solvate.

The present disclosure further includes co-crystals of Encequidar (HM-30181A) mesylate and an additional component.

The present disclosure includes a co-crystal of Encequidar (HM-30181A) mesylate and R-mandelic acid. The co-crystal of Encequidar (HM-30181A) mesylate and R-mandelic acid can be characterized by data selected from one or more of the following: a PXRD pattern having peaks at 7.9, 9.2, 13.8, 15.6 and 18.0 degrees 2-theta±0.2 degrees 2-theta; a PXRD pattern as depicted in FIG. 5; or combinations of these data.

The co-crystal of Encequidar (HM-30181A) mesylate and R-mandelic acid may be further characterized by a PXRD pattern having peaks at 7.9, 9.2, 13.8, 15.6 and 18.0 and 25.0 degrees 2-theta±0.2 degrees 2-theta, and also having one, two, three, four or five additional peaks at 10.6, 11.9, 19.0, 19.8, 22.8 and 26.3 degrees 2-theta±0.2 degrees 2-theta.

In embodiments, the molar ratio between the Encequidar (HM-30181A) mesylate and the R-mandelic acid is between 1:1.5 and 1.5:1, in some embodiments between 1:1.25 and 1.25:1, in other embodiments about 1:1.

The co-crystal of Encequidar (HM-30181A) mesylate and R-mandelic acid may be further characterized by a PXRD pattern having peaks at 7.9, 9.2, 10.6, 11.9, 13.8, 15.6 and 18.0, 19.0, 19.8, 22.8, 25.0, 26.3 degrees 2-theta±0.2 degrees 2-theta.

The co-crystal of Encequidar (HM-30181A) mesylate and R-mandelic acid may be characterized by each of the above characteristics alone or by all possible combinations, e.g., by a PXRD pattern having peaks at 7.9, 9.2, 13.8, 15.6 and 18.0 degrees 2-theta±0.2 degrees 2-theta and a PXRD pattern as depicted in FIG. 5.

The present disclosure includes a co-crystal of Encequidar (HM-30181A) mesylate and nicotinamide. The co-crystal of Encequidar (HM-30181A) mesylate and nicotinamide can be characterized by data selected from one or more of the following: a PXRD pattern having peaks at 7.8, 15.0, 15.3, 19.7 and 24.5 degrees 2-theta±0.2 degrees 2-theta; a PXRD pattern as depicted in FIG. 6; or combinations of these data.

The co-crystal of Encequidar (HM-30181A) mesylate and nicotinamide may be further characterized by a PXRD pattern having peaks at 7.8, 15.0, 15.3, 19.7 and 24.5 degrees 2-theta±0.2 degrees 2-theta, and also having one, two, three, four or five additional peaks at 6.0, 12.0, 12.7, 18.9 and 23.1 degrees 2-theta±0.2 degrees 2-theta.

In embodiments, the molar ratio between the Encequidar (HM-30181A) mesylate and the nicotinamide is between 1:1.5 and 1.5:1, in some embodiments between 1:1.25 and 1.25:1, in other embodiments about 1:1.

The co-crystal of Encequidar (HM-30181A) mesylate and nicotinamide may alternatively be characterized by a PXRD pattern having peaks at 6.0, 7.8, 12.0, 12.7, 15.0, 15.3, 18.9, 19.7, 23.1 and 24.5 degrees 2-theta±0.2 degrees 2-theta.

The co-crystal of Encequidar (HM-30181A) mesylate and nicotinamide may be characterized by each of the above characteristics alone or by all possible combinations, e.g., by a PXRD pattern having peaks at 7.8, 15.0, 15.3, 19.7 and 24.5 degrees 2-theta±0.2 degrees 2-theta and a PXRD pattern as depicted in FIG. 6.

The present disclosure further includes a co-crystal of Encequidar (HM-30181A) mesylate and citric acid. The co-crystal of Encequidar (HM-30181A) mesylate and citric acid can be characterized by data selected from one or more of the following: a PXRD pattern having peaks at 10.9, 12.7, 15.1, 19.3 and 26.8 degrees 2-theta±0.2 degrees 2-theta; a PXRD pattern as depicted in FIG. 7; or combinations of these data.

The co-crystal of Encequidar (HM-30181A) mesylate and citric acid may be further characterized by a PXRD pattern having peaks at 10.9, 12.7, 15.1, 19.3 and 26.8 degrees 2-theta±0.2 degrees 2-theta, and also having one, two, three, four or five additional peaks at 7.6, 8.3, 11.3, 11.6 and 13.3 degrees 2-theta±0.2 degrees 2-theta.

In embodiments, the molar ratio between the Encequidar (HM-30181A) mesylate and the citric acid is between 1:1.5 and 1.5:1, in some embodiments between 1:1.25 and 1.25:1, in other embodiments about 1:1.

The co-crystal of Encequidar (HM-30181A) mesylate and citric acid may alternatively be characterized by a PXRD pattern having peaks at 7.6, 8.3, 11.3, 10.9, 11.6, 12.7, 13.3, 15.1, 19.3 and 26.8 degrees 2-theta±0.2 degrees 2-theta.

The co-crystal of Encequidar (HM-30181A) mesylate and citric acid may be characterized by each of the above characteristics alone or by all possible combinations, e.g., by a PXRD pattern having peaks at 10.9, 12.7, 15.1, 19.3 and 26.8 degrees 2-theta±0.2 degrees 2-theta and a PXRD pattern as depicted in FIG. 7.

The present disclosure also provides the use of the solid state forms and co-crystals of HM-30181A base and Encequidar (HM-30181A) mesylate and of the present disclosure for preparing different solid state forms of Encequidar (HM-30181A), salts and co-crystals of Encequidar (HM-30181A), and solid state forms thereof.

The present disclosure further encompasses processes for preparing solid state forms and co-crystals of Encequidar (HM-30181A) base and Encequidar (HM-30181A) mesylate of the present disclosure. The disclosure further includes processes for preparing different solid state forms of Encequidar (HM-30181A) base and salts or co-crystals of Encequidar (HM-30181A) and solid state forms thereof. The process includes preparing at least one of the solid state forms of Encequidar (HM-30181A) base, Encequidar (HM-30181A) mesylate or of Encequidar (HM-30181A) co-crystal of the present disclosure, and converting it to different solid state forms of Encequidar (HM-30181A) base or Encequidar (HM-30181A) mesylate, or to solid state forms of or different salts or co-crystals of Encequidar (HM-30181A). The conversion to Encequidar (HM-30181A) salt can be done, for example, by a process including reacting at least one of the obtained solid state forms of Encequidar (HM-30181A) base with an appropriate acid to obtain HM-30181A acid addition salt, or basifying Encequidar (HM-30181A) mesylate to obtain Encequidar (HM-30181A) base and thereafter reacting it with appropriate acid to obtain Encequidar (HM-30181A) acid addition salt.

In another embodiment the present disclosure encompasses the above solid state forms and co-crystals of Encequidar (HM-30181A) base and Encequidar (HM-30181A) mesylate for use in the preparation of pharmaceutical compositions and/or formulations, in some embodiments for the treatment of cancer, or in some embodiments for the treatment of metastatic breast cancer and/or gastric cancer. The said pharmaceutical compositions and/or formulations can be as a combination with additional active agents, such as Paclitaxel.

In another embodiment the present disclosure encompasses the use of the above described solid state forms and co-crystals of Encequidar (HM-30181A) base and Encequidar (HM-30181A) mesylate for the preparation of pharmaceutical compositions and/or formulations, particularly as a combination with additional active agents, such as Paclitaxel.

The present disclosure further provides pharmaceutical compositions including solid state forms and co-crystals of Encequidar (HM-30181A) base and Encequidar (HM-30181A) mesylate of the present disclosure. In some embodiments, the said pharmaceutical compositions is a combination with additional active agents, such as Paclitaxel.

In yet another embodiment, the present disclosure encompasses pharmaceutical formulations including solid state forms and co-crystals of Encequidar (HM-30181A) base and Encequidar (HM-30181A) mesylate of the present disclosure, and at least one pharmaceutically acceptable excipient. In particular embodiments, the said pharmaceutical compositions is a combination with additional active agents, such as Paclitaxel.

Pharmaceutical formulations of the present disclosure contain any one or a combination of the solid state forms and co-crystals of Encequidar (HM-30181A) base and Encequidar (HM-30181A) mesylate of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, the active ingredient and any other solid excipients may be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

In embodiments, a pharmaceutical formulation of Encequidar (HM-30181A) mesylate is formulated for administration to a mammal, such as a human. Encequidar (HM-30181A) mesylate can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present disclosure encompasses a process to prepare said formulations of solid state forms and co-crystals of Encequidar (HM-30181A) base and Encequidar (HM-30181A) mesylate thereof by combining the solid state forms of Encequidar (HM-30181A) mesylate according to the present disclosure and at least one pharmaceutically acceptable excipient. The process can further include adding additional active agent, such as Paclitaxel.

Solid state forms and co-crystals of Encequidar (HM-30181A) base and Encequidar (HM-30181A) mesylate as defined herein, as well as the pharmaceutical compositions or formulations of Encequidar (HM-30181A) base and Encequidar (HM-30181A) mesylate and co-crystals thereof can be used as medicaments, in some embodiments for the treatment of cancer, or in some embodiments for the treatment of metastatic breast cancer and/or gastric cancer. In particular, it is used as a combination with additional active agents, such as Paclitaxel.

The present disclosure also provides a method of treating cancer, or a method of treating metastatic breast cancer and/or gastric cancer, by administering a therapeutically effective amount of any one or a combination of the solid state forms and co-crystals of Encequidar (HM-30181A) base and Encequidar (HM-30181A) mesylate prepared according to the present disclosure, or at least one of the above pharmaceutical compositions or formulations, optionally in a form of a combination with additional active agents, such as Paclitaxel, to a subject suffering from cancer or to a subject suffering from metastatic breast cancer and/or gastric cancer, or otherwise in need of the treatment.

The present disclosure also provides the use of solid state forms and co-crystals of Encequidar (HM-30181A) base and Encequidar (HM-30181A) mesylate, or at least one of the above pharmaceutical compositions or formulations for the manufacture of a medicament for treating cancer or for the manufacture of a medicament for treating metastatic breast cancer and/or gastric cancer. Optionally, the medicament is a combination with additional active agents, such as Paclitaxel.

The present disclosure further provides a synthetic process for preparing Encequidar (HM-30181A), which is highly efficient, and provides the final product in high yield and quality.

The present disclosure provides a process for preparing Encequidar (HM-30181A) by reacting 2-(2-(4-(2-(6,7-dimethoxy-3,4-dihydroisoquinolin-2(1H)-yl)ethyl)phenyl)-2H-tetrazol-5-yl)-4,5-dimethoxyaniline of Formula 2 and 4-oxo-4H-chromene-2-carboxylic acid of Formula 1 in the presence of oxalyl chloride or thionyl chloride:

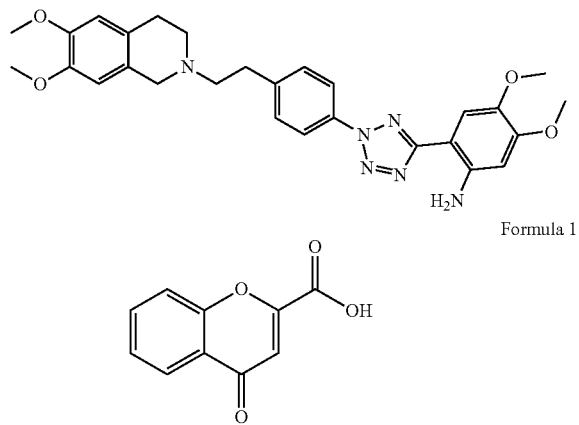

Formula 2

Formula 1

To aid the reaction, a catalytic amount of dimethylformamide ("DMF") may be used. In embodiments an amount of from about 0.05 equivalent to about 0.5 equivalent of DMF is used relative to the compound of Formula 1. The process may be performed in a presence of solvent, such as an aprotic solvent, such as tetrahydrofuran ("THF"), dichloromethane ("DCM") or mixtures thereof. The process may in some embodiments be performed in the presence of a mixture of DCM and THF.

The reaction may be performed at ambient temperatures, such as at room temperature, or from room temperature to about 60° C., in embodiments from room temperature to about 40° C.

In one particular embodiment, there is provided a process for preparing Encequidar (HM-30181A) comprising reacting 2-(2-(4-(2-(6,7-dimethoxy-3,4-dihydroisoquinolin-2 (1H)-yl)ethyl)phenyl)-2H-tetrazol-5-yl)-4,5-dimethoxyaniline of Formula 2:

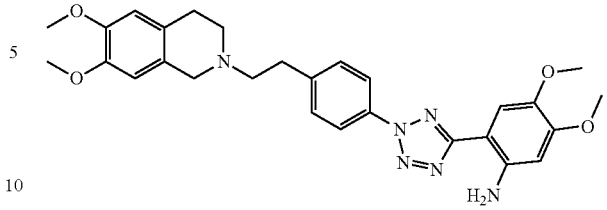

Formula 2 and 4-oxo-4H-chromene-2-carboxylic acid chloride of Formula 1A:

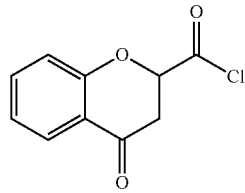

Formula 1A in the presence of a polar aprotic solvent, and optionally in the presence of a base.

The reaction may be conducted in a ratio of formula 2 to formula 1A of about 1:1 to about 1:1.5 mole equivalents, about 1:1 to about 1:1.2 mole equivalents, or about 1:1 to about 1:1.1 mole equivalents.

The reaction may be conducted at a temperature of from about 10° C. to about 40° C., about 15° C. to about 30° C., or about 20° C. to about 25° C. The reaction may be carried out under an inert atmosphere, e.g. under nitrogen or argon.

In some embodiments the polar aprotic solvent may be dichloromethane or tetrahydrofuran (THF) or combinations thereof. In embodiments, the reaction may be carried out in dichloromethane.

The reaction may be carried out in the presence of a catalytic amount of dimethylformamide ("DMF"). In embodiments an amount of from about 0.05 equivalent to about 0.5 equivalent of DMF relative to the compound of Formula I is used.

In embodiments, the process is carried out in the presence of a base, such as an inorganic base or an organic base. The inorganic base can be an alkali metal carbonate (for example, sodium carbonate, potassium carbonate, sodium hydrogen carbonate, or potassium hydrogen carbonate), an alkali earth metal carbonate, and/or an organic base, for example, an organic amine such as a tertiary amine (such as triethylamine or diisopropylethylamine).

In embodiments of the above process, the acid chloride of Formula 1A is prepared by reacting the compound of formula I with oxalyl chloride or thionyl chloride. The reaction may be carried out in a polar aprotic solvent, such as THF or DCM or combinations thereof. In some embodiments, the polar aprotic solvent is selected from DCM and THF, optionally in combination. The reaction may be conducted at a temperature of from about 10° C. to about 40° C., about 15° C. to about 30° C., or about 20° C. to about 25° C. The reaction may be carried out under an inert atmosphere, e.g., under nitrogen or argon.

In another aspect the present invention provides a process for preparing Encequidar comprising the steps of:

(1) reacting the compound of formula I with oxalyl chloride or thionyl chloride in a first polar aprotic solvent, such as THF or DCM, or combinations thereof, to prepare a compound of formula 1A;
(2) optionally removing the solvent from the compound of formula 1A;
(3) reacting the compound of formula 1A from step (1) or step (2) with the compound of formula 2, optionally in the presence of a base; and optionally in the presence of a second polar aprotic solvent, to form Encequidar.

Steps (1) and (3) may be carried out as described in any of the above embodiments. In embodiments, the process is conducted in one pot, i.e., without purification of the compound of formula 1A. For example, the compound of formula 1A, either in solution from step 1 or after solvent removal step 2, may be directly reacted with the compound of formula (2) without a separate purification procedure. The first and second polar aprotic solvents may be the same or different, and may, for example, be selected from THF and/or DCM, or other polar aprotic solvents.

In any embodiment of the present invention described herein, after the reaction is completed, Encequidar (HM-30181A) can be isolated, for example by crystallization. The crystallization may be done from a mixture of DCM, acetone and methanol; or alternatively from DMF. The isolated Encequidar (HM-30181A) can be converted to other solid state forms, co-crystals and salts, such as mesylate salt.

The processes described herein can further include converting Encequidar (HM-30181A) to a pharmaceutically acceptable salt, such as mesylate, and/or to co-crystals, solvates and crystalline forms.

The present disclosure further provides a process for preparing amorphous Encequidar (HM-30181A) mesylate. The process comprises precipitating amorphous Encequidar (HM-30181A) mesylate from a mixture comprising acetic acid and methyl tert-butyl ether ("MTBE").

In embodiments, the process comprises combining a solution of Encequidar (HM-30181A) in acetic acid with methanesulfonic acid, to obtain a solution; and combining the solution with an anti-solvent MTBE to obtain a mixture, from which amorphous Encequidar (HM-30181A) mesylate precipitates. Typically, this process is performed at room temperature.

In embodiments, combining the solution of Encequidar (HM-30181A), methanesulfonic acid and acetic acid with MTBE is done by reverse addition, i.e., the said solution is added to MTBE, typically it is added in a drop-wise manner. The addition may be done with stirring. The obtained mixture can then be further stirred, in embodiments for a sufficient time to precipitate solid Encequidar (HM-30181A) mesylate, in embodiments it is stirred for a period of about 30 minutes to about 4 hours, about 45 minutes to about 2 hours, or about an hour.

The obtained solid may be isolated, preferably by filtration. The filtered solid may be dried, for example under vacuum, at a pressure such as 300 mbar. Vacuum drying may be done at a temperature such as about 80° C., for a sufficient period, in embodiments for about 5 hours.

Having described the solid state forms and co-crystals of Encequidar (HM-30181A) base and Encequidar (HM-30181A) mesylate with reference to certain exemplary embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

Powder X-Ray Diffraction Pattern ("PXRD") Method:

Sample is powdered in a mortar and pestle and applied directly on a silicon plate holder. The X-ray powder diffraction pattern was measured with Philips X'Pert PRO X-ray powder diffractometer, equipped with Cu irradiation source=1.54184 Å (Ångström), X'Celerator (2.022° 2θ) detector. Scanning parameters: angle range: 3-40 deg., step size 0.0167, time per step 37 seconds, continuous scan.

Fourier-Transform Infrared ("FTIR") Method:

FT-IR spectra were recorded on a Nicolet 6700 FT-IR spectrometer operating in the range 4000-400 cm−1, equipped with KBr beamsplitter and DTGS detector. 16 scans were recorded at resolution of 4.0 cm−1. Samples were prepared as a KBr pellet. Empty sample compartment was used for background spectrum acquisition.

Thermogravimetric Analysis ("TGA") Method:

TGA measurements were done using TA Instruments Discovery, TG unit. 5-10 mg of sample was weighed in open aluminum pan. Sample was purged with 50 ml/min of nitrogen flow and heated in the range of 25-300° C., with heating rate of 10° C./min.

EXAMPLES

Preparation of Starting Material:

Encequidar (HM-30181A) and Encequidar (HM-30181A) mesylate can be prepared according to any procedure known in the art, for example the procedures described in International Publication No. WO 2005/033097 or in International Publication No. WO 2011/087316.

Amorphous Encequidar (HM-30181A) mesylate can be prepared by any known method for preparing amorphous materials, such as lyophilization, spray dry, fast evaporation, etc.

For example, crude Encequidar (HM-30181A) mesylate salt (about 3 grams) was dissolved in 100 mL of chloroform at room temperature, then it was filtered. The solvent was evaporated under reduced pressure (200 mbar) at 60° C. The obtained solid was analyzed by PXRD, and an amorphous solid was obtained. PXRD is shown in FIG. 1.

Alternatively, Encequidar (HM-30181A) can be prepared by the efficient procedure of the present disclosure, as detailed in Example A.

Example A

Preparation of Encequidar (HM-30181A)

4-oxo-4H-chromene-2-carboxylic acid (Formula 1) (0.5 grams; 2.63 mmol) and DMF (0.101 ml) were mixed in THF (15 ml) to form a mixture. Thiony chloride (0.21 ml; 2.89 mmol) was added to the mixture under Argon atmosphere. The mixture was stirred for 4 hours at room temperature. The solvents were removed by distillation and DCM was added (25 ml). 2-(2-(4-(2-(6,7-dimethoxy-3,4-dihydroisoquinolin-2(1H)-yl)ethyl)phenyl)-2H-tetrazol-5-yl)-4,5-dimethoxyaniline (Formula 2) (1.12 grams; 2.37 mmol) and a suspension was formed. Then, Triethylamine ("TEA", 0.58 ml; 4.21 mmol) was added and a solution was formed and further stirred for 1 hour at room temperature under Argon atmosphere. Then, acetone (15 ml), methanol (10 ml) and water (3 ml) were added to the reaction mixture and the pH was adjusted to 9.2. The obtained suspension was stirred at room temperature and the solid was filtered, washed with acetone and dried in vacuum oven yielding the product (1.5 grams).

Example 1

Preparation of Crystalline of Encequidar (HM-30181A) Mesylate—Form A

Amorphous Encequidar (HM-30181A), mesylate salt (300 mg) was suspended in toluene (30 mL) and the mixture was heated to reflux over a period of about 5 hours, using Dean-Stark apparatus by which about 5 mL of fluid was removed. The mixture was cooled down to room temperature, filtered and dried in a stream of nitrogen gas. The obtained solid was analyzed by PXRD, and a crystalline solid was obtained, designated Form A. PXRD is shown in FIG. 2.

Example 2

Preparation of Crystalline of Encequidar (HM-30181A) Mesylate—Form B

Crude Encequidar (HM-30181A), mesylate salt (500 mg) was dissolved in chloroform (10 mL) at temperature of about 40° C. Toluene (50 mL) was added to the solution while stirring and the mixture was heated to reflux over a period of several hours, using a Dean-Stark apparatus by which about 40 mL of fluid was removed. The mixture was then cooled down to room temperature, filtered and the obtained solid was dried on air. The obtained solid was analyzed by PXRD, and a crystalline solid was obtained, designated Form B. PXRD is shown in FIG. 3.

Example 3

Preparation of Crystalline of Encequidar (HM-30181A) Base—Form I

Crude Encequidar (HM-30181A), base (20 mg) was dissolved in dimethylformamide ("DMF", 0.4 mL) at about room temperature. The obtained solution was maintained in an open vial for 5 days at room temperature, and the solvent was evaporated. Then, the obtained solid was filtered and was dried on air. The obtained solid was analyzed by PXRD, and a crystalline solid was obtained, designated Form I. PXRD is shown in FIG. 4.

Example 4

Preparation of Co-Crystal of Encequidar (HM-30181A) Mesylate and R-Mandelic Acid Encequidar (HM-30181A) mesylate salt (Amorphous, 500 mg) was slurried in acetonitrile (5 mL) with R-mandelic acid (194 mg, 2 eq) for four days at room temperature. The obtained solid was filtered, washed with diethyl-ether (5 mL) and was dried on air. The obtained solid was analyzed by NMR (1:1) and PXRD. PXRD pattern is shown in FIG. 5.

Example 5

Preparation of Co-Crystal of Encequidar (HM-30181A) Mesylate and Nicotinamide Encequidar (HM-30181A) mesylate salt (Amorphous, 200 mg) was slurried in ethyl-acetate (5 mL) with nicotinamide (31 mg, 1 eq) for four days at 45° C. The obtained solid was filtered and dried on air. The obtained solid was analyzed by NMR (1:1) and PXRD. PXRD pattern is shown in FIG. 6.

Example 6

Preparation of Co-Crystal of Encequidar (HM-30181A) Mesylate and R-Citric Acid Encequidar (HM-30181A) mesylate salt (Amorphous, 500 mg) was slurried in acetone (5 mL) with citric acid (192 mg 1.6 eq) for four days at room temperature. The obtained solid was filtered and dried on air. The obtained solid was analyzed by NMR (1:1) and PXRD. PXRD pattern is shown in FIG. 7.

Example 7

Preparation of Encequidar (HM-30181A) Mesylate Form Y

Encequidar (HM-30181A) mesylate (500 mg) was suspended in toluene (20 mL) at a temperature of about 60° C. Then, acetic acid (5 mL) was added to the suspension and a solution was formed. The obtained solution was heated to the boiling point (about 110° C.) and stirred for a period of about 1 hour. Then, it was cooled down to room temperature and the obtained solid was isolated by vacuum filtration and was dried on air. The obtained solid was analyzed by PXRD, Form Y was obtained. PXRD pattern is shown in FIG. 8. HPLC(acetic acid=6.2%).

Example 8

Preparation of Encequidar (HM-30181A) Mesylate Form Y

Encequidar (HM-30181A) free base (1.0 g) was dissolved in a mixture of toluene (12 mL) and acetic acid (3 mL) at a temperature of about 80° C. and a solution formed. Methanesulfonic acid (89 µL, 1.0 eq) in toluene (5 mL) was added dropwise to the solution and a suspension was obtained. The suspension was stirred at a temperature of about 80° C. for a period of about 1 hour. The solid was isolated by vacuum filtration at temperature of about 70° C. and was dried on air. The obtained solid was analyzed by PXRD, Form Y was obtained.

Example 9

Preparation of Encequidar (HM-30181A) Mesylate Form J

Encequidar (HM-30181A) mesylate (5 mg, Form Y) was placed in a DSC sample holder. The sample was heated to a temperature of about 200° C. (10° C./min) for 10 minutes, cooled down to room temperature and the obtained solid analyzed by PXRD. Form J was obtained, PXRD pattern is shown in FIG. 9.

Example 10

Preparation of Encequidar (HM-30181A) Mesylate Form B

Encequidar (HM-30181A) free base (0.5 grams) was dissolved in a mixture of toluene (11 mL) and acetonitrile (4 mL) at a temperature of about 80° C. and a solution was formed. The solution was seeded with Encequidar (HM-30181A) mesylate Form B (25 mg, 5%) and a suspension was formed. Methanesulfonic acid (45 µL, 1.0 eq) in acetonitrile (1 mL) was added dropwise to the suspension at 80° C., heated to the boiling point (85° C.-110°) and the solvents were removed by distillation. Toluene (10 mL) and Encequidar (HM-30181A) mesylate Form B (25 mg, 5%) were added and the mixture was stirred for a period of about 4 hours at a temperature of about 90° C. The mixture was cooled down to room temperature and the obtained solid isolated by vacuum filtration and was dried on air. The obtained isolated solid was analyzed by PXRD, Form B was obtained.

Example 11

Preparation of Amorphous Encequidar (HM-30181A) Mesylate

Encequidar (HM-30181A) free base (1.0 gram) was dissolved in acetic acid at room temperature (10 mL) and methanesulfonic acid (95 µL, 1.0 eq) was added dropwise. The obtained solution was added dropwise to MTBE (40 mL), upon stirring. Additional amount of MTBE (50 mL) was added to the obtained mixture and the mixture was stirred for a period of about 1 hour. The obtained solid was isolated by vacuum filtration and vacuum dried (80° C., 300 mbar, 5 hours). The obtained solid was analyzed by PXRD, amorphous was obtained.

Example 12

Preparation of Encequidar (HM-30181A) Mesylate Form E

Encequidar (HM-30181A) mesylate (30 mg) and methanol (1 mL) were charged into a glass vial and the vial was closed. The obtained mixture was heated to a temperature of about 60° C. and was stirred until the solid completely dissolved. The obtained solution was cooled to room temperature and the obtained gel-like material was left to stand in the solvent for several days. After several days the obtained yellow powder was isolated by filtration and dried on air. The obtained solid was analyzed by PXRD, Form E was obtained. PXRD pattern is shown in FIG. 10.

Example 13

Preparation of Encequidar (HM-30181A)

Step 1: Preparation of Formula 1A:
Thionyl chloride (0.84 ml; 11.57 mmol; 1,1 eq) was added to a mixture of compound of Formula 1 (2.0 grams; 10.52 mmol), DCM (40 ml) and DMF (0.081 ml; 1.05 mmol; 0.1 eq), under Argon atmosphere. The obtained mixture was stirred at a temperature of about 40° C. for a period of about 5 hours and then it was further stirred at room temperature overnight.
Step 2: Preparation of Encequidar (HM 30181A):
A solution of compound of formula 2 (5.64 grams; 10.52 mmol) in DCM (80 ml) was added to the mixture of Formula 1A obtained in the previous step, using a cannula. A suspension formed. Then, DCM was distilled off and acetone (80 ml) and water (20 ml) were added, and a suspension formed. The pH of the suspension was adjusted to 9-10 using NaOH (2M) and the suspension was filtered. The obtained crystals were washed with water (2×40 ml) and then it was washed with acetone (2×40 ml). The product was dried at temperature of about 50° C. for 6 hours in a vacuum oven yielding 7.22 grams of the product (Yield=88.66%).

The invention claimed is:

1. Crystalline Form B of Encequidar (HM-30181A) mesylate, characterized by a PXRD pattern comprising peaks at 6.4, 7.6, 9.5, 14.6, 17.9, 18.7, 22.8, and 25.0 degrees 2-theta±0.2 degrees 2-theta.

2. Crystalline Form B of Encequidar (HM-30181A) mesylate according to claim 1, further comprising one, two or three additional peaks at 4.6, 10.0, or 15.4 degrees 2-theta±0.2 degrees 2-theta.

3. Crystalline Form B of Encequidar (HM-30181A) mesylate according to claim 1, which contains no more than about 20% of any other crystalline forms of Encequidar (HM-30181A) mesylate.

4. Crystalline Form B of Encequidar (HM-30181A) mesylate according to claim 1, which contains no more than about 20% of amorphous Encequidar (HM-30181A) mesylate.

5. A pharmaceutical composition comprising crystalline Form B of Encequidar (HM-30181A) mesylate according to claim 1.

6. A pharmaceutical formulation comprising crystalline Form B of Encequidar (HM-30181A) mesylate according to claim 1, or a pharmaceutical composition of claim 5, and at least one pharmaceutically acceptable excipient.

7. The pharmaceutical composition of claim 5, wherein the pharmaceutical composition or formulation is in combination with additional active agents, and optionally wherein the additional active agent comprises Paclitaxel.

8. A process for preparing a pharmaceutical formulation comprising combining a crystalline Form B of Encequidar (HM-30181A) mesylate according to claim 1, with at least one pharmaceutically acceptable excipient.

9. A method of treating cancer, optionally for treating metastatic breast cancer and/or gastric cancer, comprising administering a therapeutically effective amount of crystalline Form B of Encequidar (HM-30181A) mesylate according to claim 1 to a subject in need of the treatment, in combination with additional active agents, and optionally wherein the additional active agent comprises Paclitaxel.

10. A process for preparing an Encequidar (HM-30181A) salt or a solid state form thereof comprising preparing crystalline Form B of Encequidar (HM-30181A) mesylate according to claim 1, and converting it to another Encequidar (HM-30181A) salt, co-crystal or a solid state form thereof.

11. A process for preparing amorphous Encequidar (HM-30181A) mesylate comprising precipitating amorphous Encequidar (HM-30181A) mesylate from a mixture comprising acetic acid and methyl tert-butyl ether ("MTBE").

12. The process according to claim 11, comprising:
 a. combining Encequidar (HM-30181A) in acetic acid with methanesulfonic acid to obtain a solution;
 b. combining the solution with MTBE to obtain a mixture;
 c. isolating the obtained solid; and optionally
 d. drying the solid.

13. The process according to claim 12, wherein step b comprises adding the solution of Encequidar (HM-30181A) in acetic acid to MTBE.

14. The process according to claim 11, further comprising combining the amorphous Encequidar (HM-30181A) with at least one pharmaceutically acceptable excipient to prepare a pharmaceutical composition or formulation.

\* \* \* \* \*